United States Patent [19]
Whitehead

[11] Patent Number: 4,879,029
[45] Date of Patent: Nov. 7, 1989

[54] LIQUID CHROMATOGRAPH APPARATUS

[75] Inventor: Martin A. Whitehead, Landbeach, England

[73] Assignee: U.S. Philips Corporation, New York, N.Y.

[21] Appl. No.: 339,938

[22] Filed: Apr. 18, 1989

[30] Foreign Application Priority Data

Sep. 17, 1986 [GB] United Kingdom ............... 8622328

[51] Int. Cl.[4] ........................................... B01D 15/08
[52] U.S. Cl. ............................... 210/198.2; 210/101; 138/30; 417/543
[58] Field of Search ................... 417/540, 542, 543; 210/101, 198.2; 138/30

[56] References Cited

U.S. PATENT DOCUMENTS

| | | | |
|---|---|---|---|
| 1,364,680 | 1/1921 | Barton | 417/543 |
| 1,553,768 | 9/1925 | Gleason | 417/543 |
| 1,774,095 | 8/1930 | Hajek | 417/543 |
| 1,777,891 | 10/1930 | Pearson | 417/543 |
| 2,915,185 | 12/1959 | Waldherr | 417/543 |
| 3,442,293 | 5/1969 | Erdmann | 138/30 |
| 3,669,150 | 6/1972 | Everett | 417/543 |
| 4,000,070 | 12/1976 | Sumikama | 210/198.2 |
| 4,116,046 | 9/1978 | Stein | 210/198.2 |
| 4,128,476 | 12/1978 | Rock | 210/198.2 |
| 4,177,016 | 12/1979 | Aude | 417/539 |
| 4,541,452 | 9/1985 | Paradis | 210/198.2 |
| 4,591,442 | 5/1986 | Andrews | 210/198.2 |
| 4,595,495 | 6/1986 | Yotam | 210/198.2 |
| 4,595,496 | 6/1986 | Carson | 210/198.2 |
| 4,670,138 | 6/1987 | Yunoki | 210/198.2 |

FOREIGN PATENT DOCUMENTS 2039091 7/1980 United Kingdom ............ 210/198.2

Primary Examiner—Ernest G. Therkorn
Attorney, Agent, or Firm—Paul R. Miller

[57] ABSTRACT

Liquid chromatograph apparatus includes a solvent proportioning valve arrangement which comprises a block (21) having four inlet passages and a number of outlet passages communicating with a common outlet passage (28) and an outlet port (29) to which a tube may be attached for connection to the inlet of a pump. Each inlet passage (30) is connected to a solvent source by a tube (43) which passes into a chamber (32) mounted on the block (21). The chamber (32) is air-tight and contains a quantity of gas or air to absorb shock waves in the liquid when the diaphragm (26) blocks the inlet (30) and outlet (27) passages.

10 Claims, 4 Drawing Sheets

LIQUID CHROMATOGRAPH APPARATUS

This is a continuation of application Ser. No. 94,625, filed Sept. 9, 1987, now abandoned.

The invention relates to liquid chromatograph apparatus comprising means for selecting and feeding one or more of a plurality of solvents to the input of a reciprocating pump, means for feeding the output of the pump to a separating column, means for injecting a sample into the solvent flowing from the pump to the separating column, and a detector for detecting the separated components of the sample in the eluent from the separating column, wherein the selecting means comprises a proportioning valve arrangement having a plurality of valves, each valve having inlet means for connection to a respective one of the solvent sources and an outlet which is coupled via a common connection to the inlet of the pump.

In some applications of high performance liquid chromatography (HPLC) it is necessary to change the composition of the solvent or mobile phase in a controlled manner during the analysis. For example, in absorption chromatography it is not always possible to choose a mobile phase which will enable all of the sample components to be separated and eluted in a reasonable time. If the polarity range of the sample mixture is wide the use of a low polarity solvent as the mobile phase will give a maximum separation of the low polarity sample components but will also give long retention times for the more polar constituents. Conversely the use of a polar mobile phase will result in little or no separation of the low polarity sample components but will give short retention times for the polar materials. This problem can be overcome by the use of a technique known as gradient elution which is analogous to temperature programming as used in gas chromatography. Gradient elution involves the use of a low polarity mobile phase to separate the low polarity sample components followed by a progressive increase in solvent polarity so as to quickly elute the more polar components.

Normally gradient elution involves starting the analysis with one particular mobile phase and then adding progressively increasing amounts of a second solvent during the analysis. The composition change required may involve a linear increase in the concentration of the second solvent with time or a more complex gradient may be required. However, it may also be necessary to add more than a second solvent and in some instances third and fourth solvents may be required to be mixed to produce the desired mobile phase.

There are two main methods to obtain the changing constituents of the mobile phase when using a reciprocating piston pump to produce the flow of mobile phase to the column. The first is high pressure mixing, where the high pressure outputs of two or more pumps are combined together before being applied to the column. The individual pump flow rates are selected to give the desired composition of the solvents while the sum of their flow rates gives the desired total flow rate. The second method is to use low pressure mixing where the solvents are proportioned by a set of solenoid valves or similar devices which are switched to give the desired mixed composition. This switching or proportioning is made to happen during the suction period of a single high pressure pump and the switching device is fitted before the inlet line of the pump.

Both methods have advantages and disadvantages. When low total flow rates are in use together with low percentage mixes, high pressure mixing demands that one pump is running at a very low flow rate which is often difficult to achieve in a reproducible and reliable manner. Thus if the mix required is 99% of solvent A and 1% of solvent B then the pump supplying solvent B will be running at approximately 100th of the rate of the pump which is supplying solvent A. Further high pressure pumps are frequently controlled by means of pressure measuring devices connected at the outlet side of the pump. This can make it very difficult to connect such pumps together for high pressure mixing because of the problem of identifying which pressure measuring device is controlling which pump. Simple symmetrical methods will not work if gradient elution is employed where the solvent mixed composition varies as an arbitrary function of time during the chromatographic analysis.

Low pressure mixing has the disadvantage that the system delay volume (volume between the mixing point and the head of the chromatographic column) is larger since the whole pump volume is involved. This method, however, is not limited at low flow rates since it becomes easier at low flow rates to proportion the solvents at the inlet to the pump. However, as flow rates increase the time allowed for proportioning the solvents into the pump is steadily decreased. Further, in order to reduce pulsations of flow at the outlet of the pump, the suction time of each piston is normally made a small proportion of the total pump cycle. Thus the time for proportioning the solvents into the inlet is correspondingly reduced. As a result the valves used to proportion the solvents to the inlet of the pump have to be very quick acting. Minimising the pump suction time increases the inlet flow rates and the consequent fluid accelerations and decelerations. This may lead to outgassing, cavitation, or the piston failing to fully load due to inertia or compressibility effects on the liquid. Any of these effects produces errors in the solvent composition delivered at a particular flow rate.

It is often necessary to achieve a particular solvent composition by mixing together two or more solvents during the relatively brief refill period of the pump. This is usually achieved by opening or closing separate flow control valves for each solvent. The period that each valve is open as a fraction of the time available for piston refill determines the solvent mix which is passed into the pump. To obtain maximum accuracy it is necessary that the flow through the valves is constant. Further, it has been found that if the valves are opened and closed quickly the propagating pressure waves caused by the inertia of the flowing liquid are of sufficient magnitude to cause the valves to re-open and allow through a further amount of solvent. This causes an inaccuracy in mixing.

It is an object of the invention to provide liquid chromatograph apparatus in which solvent mixing is achieved at the inlet to the pump in which the effects of at least some of the disadvantages referred to hereinbefore are mitigated.

The invention provides liquid chromatograph apparatus as set forth in the opening paragraph, characterised in that the inlet means for each valve includes a chamber having a solvent inlet and a solvent outlet with the chamber being partially occupied by air or a gas or a mixture of gases and that the chamber is located adjacent to the valve inlet.

By providing at the inlet of the switching valve a closed chamber which contains a highly compressible material, that is air or gases, the effects of the flow inertia on closing the valve are reduced since any pressure waves are dissipated in the compression of the gases in the chamber rather than attempting to open the valves. Thus a more constant flow of the liquid during the open time of the valves and a reduction in the magnitude of the pressure waves, which now become such that they do not force the valves to bounce open, enables a much more repeatable mixture of solvent components to be obtained.

The chamber may comprise a body portion communicating with the inlet port of the valve and a cap portion through which a tube projects for passing solvent into the chamber with the cap portion being detachable from the body portion. This enables a simple arrangement for interchanging solvents.

The body portion and cap portion may have a circular section, the cap portion having a cylindrical wall, the interior of the cylindrical wall having an inclined portion at its open end such that the internal diameter of the cap portion reduces toward the top of the cap until it is close to the outer diameter of the body portion, the body portion having a step or groove for locating an O-ring and when the cap portion is assembled on the body portion the O-ring sealing the gap between the cap and body portion to retain air or gas in the chamber. With this arrangement the interior of the chamber is automatically supplied with a volume of air since as the cap portion is pushed down over the body portion it traps a volume of air in its interior which is prevented by the O-ring from escaping and thus is forced into the interior of the body portion.

Each valve inlet port may comprise a screw-threaded portion into which the body portion is screwed. This provides a simple mounting arrangement for the chamber on the valve body and ensures that the chamber is located close to the inlet port of the valve.

The plurality of valves may be formed by a corresponding plurality of inlet and outlet ports in a single block, a plurality of diaphragms arranged to be capable in a first position of isolating a respective input and output port and in a second position of allowing liquid communication between the respective inlet and outlet port, each diaphragm being movable between the first and second positions by a solenoid and the outlet ports being joined within the block to a common outlet means. This arrangement enables a compact construction which can be located close to the inlet to the pump. It is desirable that as short as possible a length of tube between the outlet of the valves and the inlet of the pump is used to minimise the delay volume of the system and minimise pressure pulsations in this tube.

BRIEF DESCRIPTION OF THE DRAWING

An embodiment of the invention will now be described, by way of example, with reference to the accompanying drawings, in which.

DESCRIPTION OF THE PREFERRED EMBODIMENTS

Figure 1:
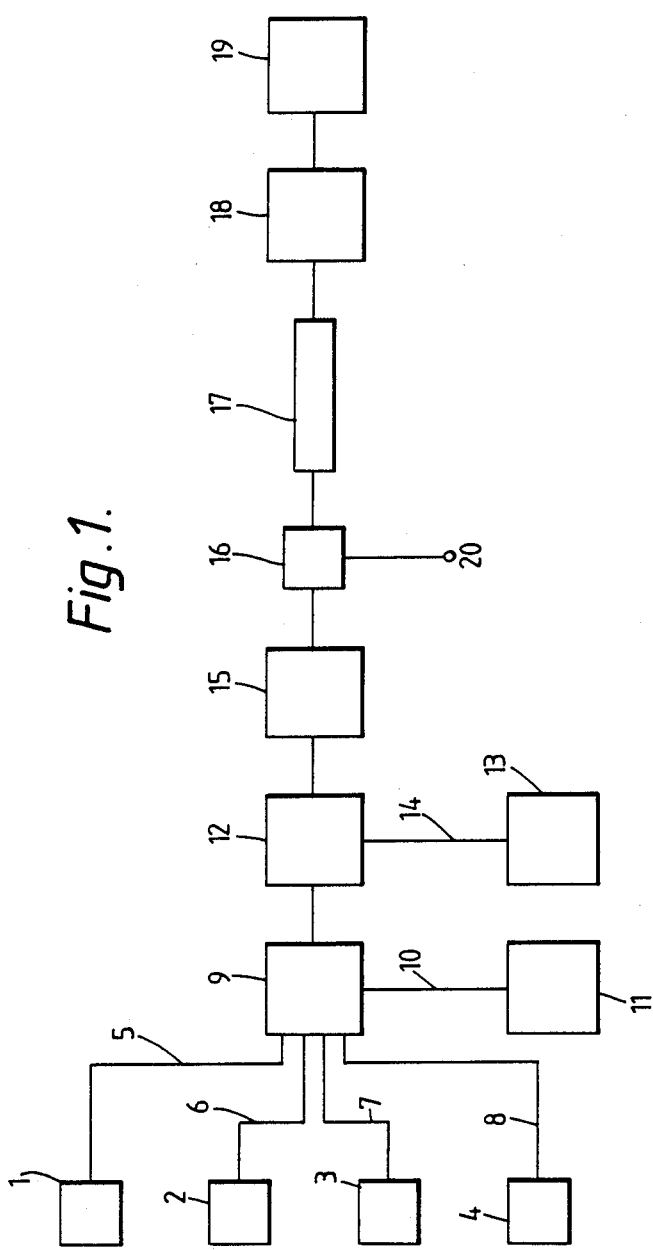
FIG. 1 shows in block schematic form a liquid chromatograph apparatus according to the invention.

The liquid chromatograph apparatus shown in FIG. 1 comprises four solvent reservoirs 1 to 4, which are fed via individual tubes 5 to 8 to the inlets of a proportioning valve arrangement 9. The proportioning valve arrangement is electrically operated and is controlled over line 10 from a solvent proportioning control arrangement 11. The outlet of the proportioning valve arrangement 9 is fed to the inlet of a pump 12. The pump 12 is controlled by means of a pump control circuit 13 over a line 14. The outlet from the pump 12 is fed to the inlet of a solvent mixer 15 whose outlet feeds a sample injection means 16. The outlet of the sample injection means 16 is fed to the input of a separating column 17 whose outlet is fed to a detector 18. The output of the detector 18 is fed to a signal processing and display arrangement 19. A second port of the sample injection means 16 is fed with a sample via a sample inlet 20.

In operation a selected solvent is fed to the pump 12 via the proportioning valve arrangement 9. The proportioning valve arrangement 9 selects each of the solvent sources 1 to 4 in proportion to the desired composition of the solvent to be fed to the pump, that is the solvent proportioning control arrangement 11 operates the appropriate valves at the appropriate times to feed 7 either a selected one of the solvents 1 to 4 or to feed in quick succession two or more solvents to the pump inlet during the suction stroke of the pump to provide a mixture of two or more solvents to be fed to the column. The pump control circuit 13 controls the speed of the pump to obtain the desired flow rate of the solvent. The solvent mixer 15 ensures that the various components of the solvent to be fed to the column are thoroughly mixed together and comprises a tapering enclosed chamber having an inlet located adjacent its larger end and an outlet located adjacent its smaller end. The solvent mixer 15 is an optional component of the system and may not be required under all operating conditions. Its use will depend on the system construction and it may be by-passed under certain conditions and ins some systems may be omitted. Further, it could be replaced by other forms of solvent mixer either static or dynamic. The proportioning valve 9 is provided, adjacent to the inlet to each valve, with a chamber having a solvent inlet and a solvent outlet, the chamber being partially occupied by air or a gas or mixture of gases. This chamber is located close to the inlet port of each valve and relatively distant from the respective solvent containing vessel 1 to 4.

Figure 2:
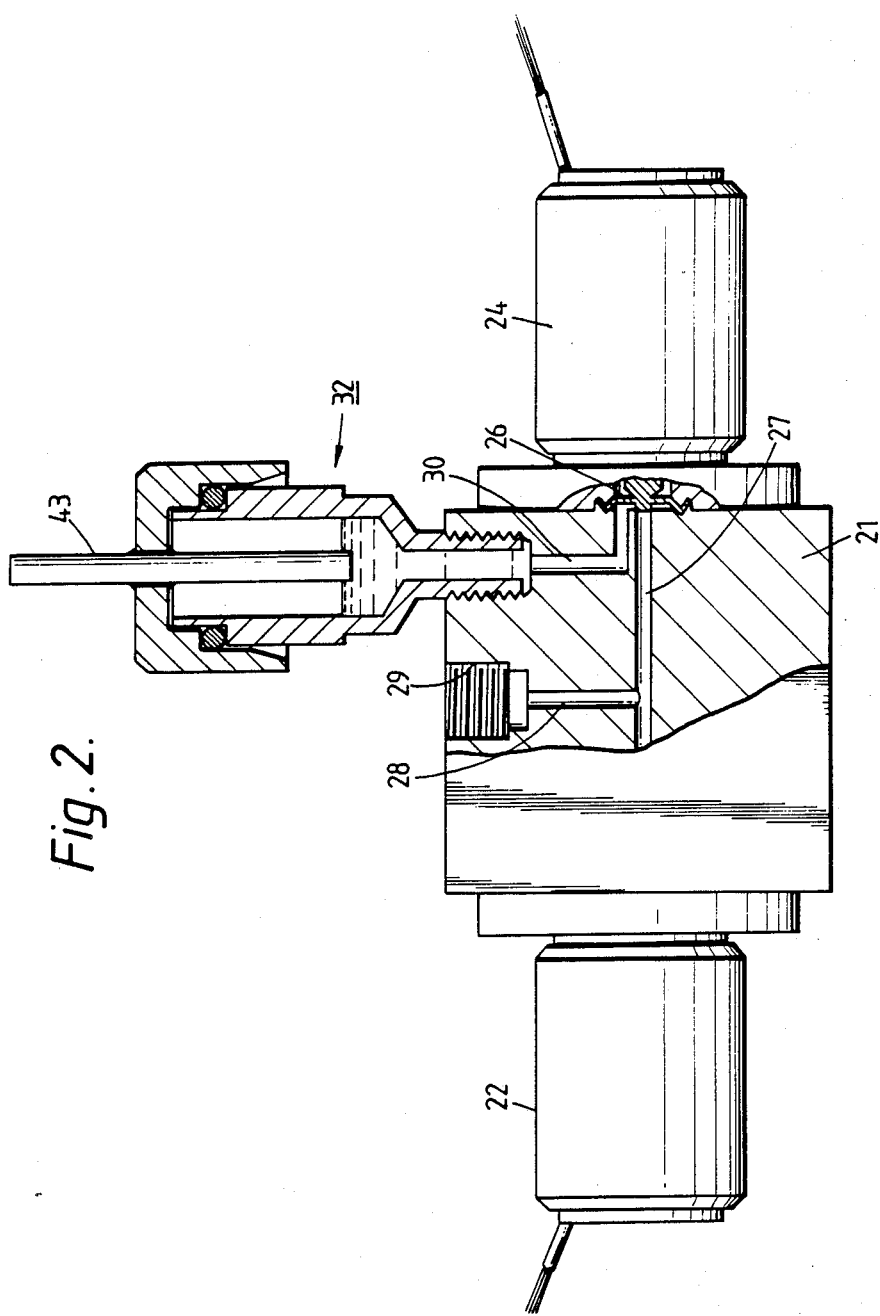
FIG. 2 is a partial cross-section side elevation of a proportioning valve arrangement for use in the chromatograph apparatus of FIG. 1.
Figure 3:
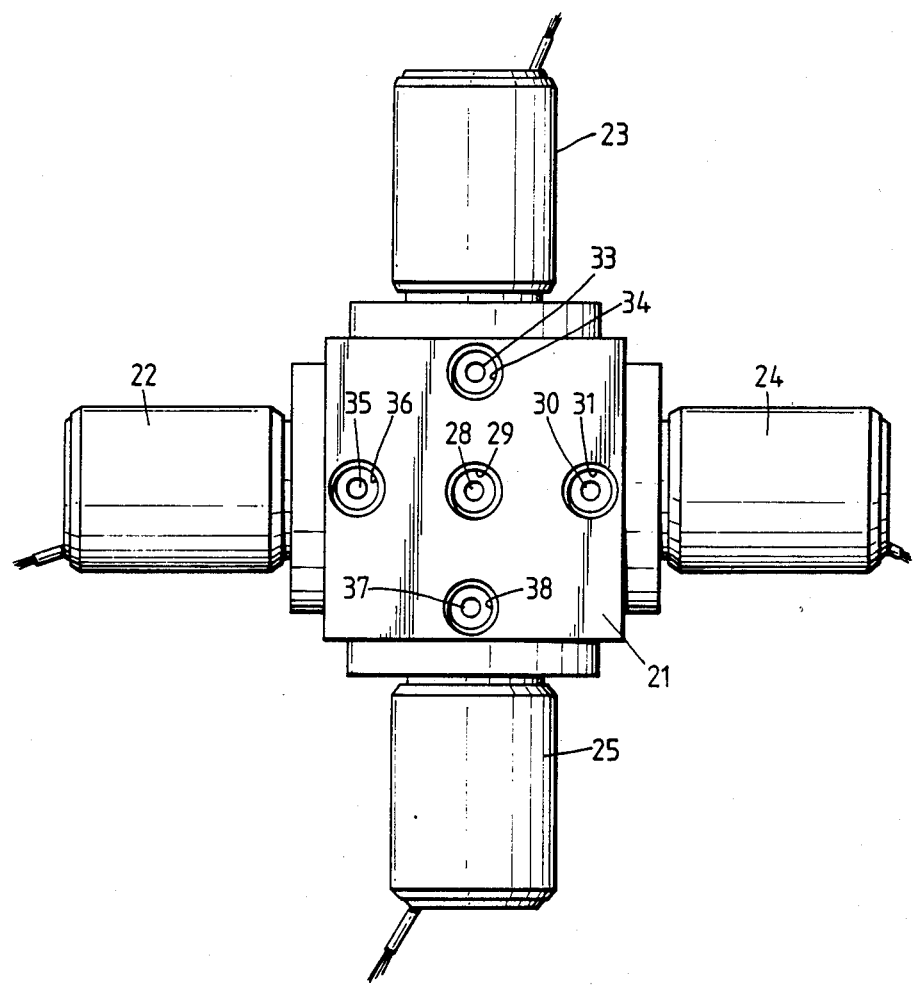
FIG. 3 is a plan view of the proportioning valve arrangement shown in FIG. 2.

The solvent proportioning valve arrangement 9 is shown in FIGS. 2 and 3, and comprises a block 21 on which are mounted four solenoids 22, 23, 24 and 25 which operate respective diaphragms one of which is shown in FIG. 2 and referenced 26. Clearly each of the solenoids operates a similar device. The valve outputs are commoned within the block 21 in a cross shaped tube 27 which feds a common upright tube 28. The tube 28 communicates with outlet means 29 which comprises a screw-threaded recess. The outlet means 29 is arranged so that a connecting tube with a connector on the end can be screwed into the outlet 29, the other end of the tube having a similar connection into the inlet of the pump. Thus all the outlet ports from the valves are commoned to a single outlet means 29. Within the block 21 the inlet means to each valve comprises a tube 30 and a recess 31 which communicates with the tube and which is screw-threaded to receive a chamber 32. For the sake of simplicity only one such chamber and one such valve are shown in FIG. 2, but it can be seen from FIG. 3 that there is a respective valve inlet for each valve, each of which contain an inlet means for mounting such a chamber. These are referenced on FIG. 3 as items 33 to 38. Thus it is ensured that the chambers one of which is shown as item 32 are located close to the inlet ports of the valves.

Figure 4:
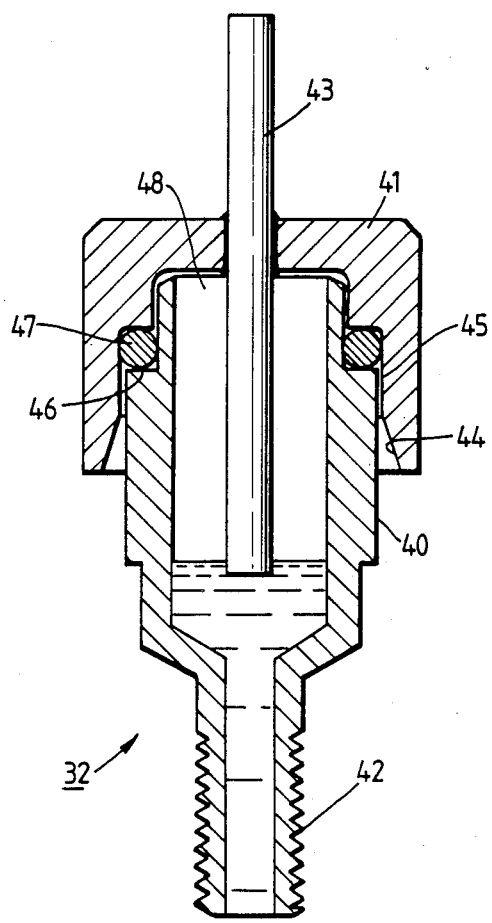
FIG. 4 is a cross-sectional elevation of a chamber forming part of the inlet means for the proportioning valve arrangement shown in FIGS. 2 and 3.

The chamber 32 is shown in greater detail in FIG. 4 and comprises a body portion 40 and a cap portion 41. The body and cap portions are both circular in section. The body portion 40 has a screw-threaded projecting portion 42 which is arranged to mate with the inlet means 31, 33, 35 and 37 of the valves in the valve block 21. The cap portion 41 has a tube 43 which passes through the cap portion into the interior of the chamber when the cap is assembled onto the body portion, the tube 43 being brazed into an aperture in the cap 41. The internal wall of the cap portion 41 has at its opening an inclined portion 44 which tapers inwardly from the free end of the wall until it meets a parallel section 45. The wall of the body portion 40 includes a step 46 on which an O-ring 47 is located. It would of course be possible to locate the O-ring by means of a groove rather than a step if desired. The O-ring 47 seals the gap between the body portion and the cap portion when the cap is assembled onto the body portion so that an enclosed chamber 48 is formed which contains either air or a gas or a mixture of gases. With this construction the act of putting the cap 41 onto the body 40 provides the chamber. If the body was already filled with liquid the chamber 48 would still contain a pocket of air when the cap was pushed down over the body since the air within the cap portion would be prevented from escaping by the O-ring 47 and push the liquid in the body chamber 48 up the pipe 43 back towards the source of solvent. Thus using this arrangement no special proceedure is required to fill the chamber with a sufficient amount of air to provide a resilient cushion to prevent the shock pressure waves from transmitting along the pipes.

Various modifications may be made to the embodiment described, for example the valves need not be solenoid operated but could for example be pneumatically operated valves. The choice of valve will depend on the operating speed required, the reliability, cost, and ease of control for any particular application. The chamber 32 may be constructed in alternative ways. The cap for example could be connected to the body portion by a screw-thread but it is necessary to ensure that a volume of air or other gas is trapped within the chamber. It is not necessary that a two part construction for the chamber is used provided that it can be ensured that a volume of air is retained within the chamber. The number of valves provided will depend on the number of solvents which it is desired to mix together and while four have been shown in this application any convenient number may be provided. The arrangement of valves round a single block provides a compact construction minimising the liquid volume between the outlets of the valve and the inlet to the pump, but other constructions could be devised which would prove satisfactory under certain system requirements. If the volume of liquid between the pump and valve outlet is not critical then a side by side arrangement of valves with a longer connecting tube from the outlets of the valves to the pump inlet may be satisfactory.

I claim:

1. A liquid chromatograph apparatus comprising
   reciprocating piston pump means for pumping solvent,
   first means for selecting and for feeding at least one of a plurality of solvents to an input of said reciprocating pump means, said first means including
   a plurality of solvent sources,
   proportioning valve means for feeding solvent to said reciprocating piston pump means, said proportioning valve means having a plurality of valves for feeding at least one of said plurality of solvents to said reciprocating pump means,
   wherein each of said valves has inlet means for connecting to at least one of said plurality of solvent sources, said inlet means for each of said valves including a chamber having a solvent inlet and a solvent outlet, said chamber being partly occupied by at least one gas, and said chamber being adjacent to said proportioning valve means, wherein said chamber structure enables constant flow of solvent to prevent irregular opening of said valves by dissipation in said gas and wherein said chamber includes a hollow body portion and a cap portion, said body portion communicating with said inlet means of said valves, said cap portion having a tube projecting from said at least one solvent sources to said body portion, said tube passing solvent from said solvent sources to said chamber, and said cap portion being detachable from said body portion, and
   wherein each of said valves has an outlet coupled to an input of said reciprocating piston pump means,
   second means for feeding an output of said reciprocating piston pump means to a separating column,
   third means for injecting a sample into said solvent flowing from said reciprocating piston pump means to said separating column, and
   detector means for detecting separated components of said sample in eluent from said separating column.

2. A liquid chromatograph apparatus according to claim 1, wherein both said body portion and said cap portion have a circular cross-section, wherein said cap portion has a cylindrical wall having an interior surface with an inclined portion at an open end, said cap portion having an internal diameter declining in size toward a top of said cap portion until said internal diameter is nearly equal to the outer diameter of said body portion, wherein said body portion has a means for locating an O-ring, and wherein when said cap portion is assembled on said body portion, said O-ring seals a gap between said cap portion and said body portion to retain air or gas in said chamber.

3. A liquid chromatograph according to claim 2, wherein said means for locating said O-ring includes one of a step portion in said body portion or a groove in said body portion.

4. A liquid chromatograph apparatus according to claim 1 or claim 2, wherein said inlet means includes a screw-threaded portion into which said body portion of said chamber is screwed.

5. A liquid chromatograph apparatus according to claim 1 or claim 2, wherein said plurality of valves include a plurality of inlet ports and outlet ports in a single block, and a plurality of diaphragms with each diaphragm being disposed to isolate a respective inlet port and outlet port in a first position and to permit liquid communication between said respective inlet port and outlet port in a second position, and wherein solenoid means are disposed for moving said plurality of diaphragms between said first position and said second position for said plurality of inlet ports and outlet ports, said plurality of outlet ports being joined in said single block to said outlet coupled to said input of said reciprocating pump means.

6. A liquid chromatograph apparatus according to claim 5, wherein said plurality of said inlet ports and said outlet ports and said plurality of said diaphragms is four.

7. A liquid chromatograph apparatus according to claim 1, wherein said plurality of valves include a plurality of inlet ports and outlet ports in a single block, and a plurality of diaphragms with each diaphragm being disposed to isolate a respective inlet port and outlet port in a first position and to permit liquid communication between said respective inlet port and outlet port in a second position, and wherein solenoid means are disposed for moving said plurality of diaphragms between said first position and said second position for said plurality of inlet ports and outlet ports, said plurality of outlet ports being joined in said single block to said outlet coupled to said input of said reciprocating pump means.

8. A liquid chromatograph apparatus according to claim 7, wherein said plurality of said inlet ports and said outlet ports and said plurality of said diaphragms is four.

9. A liquid chromatograph apparatus according to claim 1, wherein said gas is air.

10. A liquid chromatograph apparatus according to claim 1, wherein said at least one gas is a mixture of gases.

* * * * *